(12) United States Patent
Kawabata et al.

(10) Patent No.: US 11,647,928 B2
(45) Date of Patent: May 16, 2023

(54) BIOMAGNETISM MEASURING DEVICE

(71) Applicants: National University Corporation Tokyo Medical and Dental University, Tokyo (JP); TDK CORPORATION, Tokyo (JP)

(72) Inventors: Shigenori Kawabata, Tokyo (JP); Tomohiko Shibuya, Tokyo (JP); Shuichi Okawa, Tokyo (JP)

(73) Assignees: National University Corporation Tokyo Medical and Dental University, Tokyo (JP); TDK Corporation, Tokyo (JP)

( * ) Notice: Subject to any disclaimer, the term of this patent is extended or adjusted under 35 U.S.C. 154(b) by 251 days.

(21) Appl. No.: 16/306,069

(22) PCT Filed: Jun. 2, 2017

(86) PCT No.: PCT/JP2017/020574
§ 371 (c)(1),
(2) Date: Nov. 30, 2018

(87) PCT Pub. No.: WO2017/209273
PCT Pub. Date: Dec. 7, 2017

(65) Prior Publication Data
US 2019/0133477 A1 May 9, 2019

(30) Foreign Application Priority Data
Jun. 3, 2016 (JP) .............................. JP2016-112192

(51) Int. Cl.
*A61B 5/242* (2021.01)
*A61B 5/05* (2021.01)
(Continued)

(52) U.S. Cl.
CPC ................ *A61B 5/242* (2021.01); *A61B 5/05* (2013.01); *G01R 33/00* (2013.01); *A61B 5/4064* (2013.01);
(Continued)

(58) Field of Classification Search
CPC ....... A61B 5/04005; A61B 5/05; A61B 5/242; A61B 2562/046; A61B 2562/0223;
(Continued)

(56) References Cited

U.S. PATENT DOCUMENTS 8,933,696 B2   1/2015  Nishikawa
2004/0002645 A1 *  1/2004  Ewing .................... A61B 5/245
                                                        600/409
(Continued)

FOREIGN PATENT DOCUMENTS

EP   0884601 A1    12/1998
JP   H0542120 A  *  2/1993
(Continued)

OTHER PUBLICATIONS

International Search Report issued in International Application No. PCT/JP2017/020574, dated Jul. 25, 2017 (4 pages).
(Continued)

*Primary Examiner* — Chao Sheng
(74) *Attorney, Agent, or Firm* — Osha Bergman Watanabe & Burton LLP

(57) ABSTRACT

The objective of the present invention is to provide a biomagnetism measuring device with which it is possible for a magnetic sensor to be disposed in an optimal position in accordance with an object being measured. A biomagnetism measuring device (1) according to the present invention is provided with: a plurality of magnetic sensors (11) which detect biomagnetism; and a holding portion (12) in which are formed frames (13) which detachably hold the plurality (Continued)

of magnetic sensors (11) in such a way as to face a living body. Further, the biomagnetism measuring device (1) according to the present invention is provided with: a plurality of magnetic sensors (11) which detect biomagnetism; and a holding portion (12) in which are formed rails (16) which movably hold the plurality of magnetic sensors (11) in such a way as to face a living body.

12 Claims, 8 Drawing Sheets

(51) Int. Cl.
    *G01R 33/00*     (2006.01)
    *A61B 5/00*     (2006.01)

(52) U.S. Cl.
    CPC . *A61B 2562/0223* (2013.01); *A61B 2562/046* (2013.01); *A61B 2562/16* (2013.01); *A61B 2576/023* (2013.01); *A61B 2576/026* (2013.01)

(58) Field of Classification Search
    CPC ............ A61B 2562/16; A61B 5/4064; A61B 2576/023; A61B 2576/026; G01R 33/00
    See application file for complete search history.

(56) References Cited

U.S. PATENT DOCUMENTS

| | | |
|---|---|---|
| 2009/0012384 A1 | 1/2009 | Adachi et al. |
| 2009/0204195 A1* | 8/2009 | Jacobsen ................. A61B 5/24 607/148 |
| 2013/0150702 A1* | 6/2013 | Hokari ..................... A61B 5/05 600/409 |
| 2013/0317337 A1 | 11/2013 | Wu et al. |
| 2014/0062472 A1* | 3/2014 | Nishikawa ......... A61B 5/04008 324/252 |

FOREIGN PATENT DOCUMENTS

| | | | | |
|---|---|---|---|---|
| JP | 2000-051169 A | 2/2000 | | |
| JP | 2000041965 A | 2/2000 | | |
| JP | 3846675 B2 | 11/2006 | | |
| JP | 201220143 A | 2/2012 | | |
| JP | 2012095939 A | 5/2012 | | |
| JP | 2013244403 A | 12/2013 | | |
| JP | 5861703 B2 | 2/2016 | | |
| WO | WO-2011030985 A1 * | 3/2011 | ........... | G01R 33/035 |
| WO | 2014006387 A1 | 1/2014 | | |

OTHER PUBLICATIONS

Written Opinion of the International Searching Authority issued in International Application No. PCT/JP2017/020574, dated Jul. 25, 2017 (6 pages).
Liwei Chan et al: "FingerPad", Proceedings of the 26th Annual ACM Symposium on User Interface Software and Technology, UIST '13, Oct. 8, 2013 (Oct. 8, 2013), pp. 255-260 (6 pages).
Partial Supplementary European Search Report issued in European Application No. 17806823.5, dated Oct. 11, 2019 (14 pages).
Office Action issued in the counterpart European Patent Application No. 17806823.5, dated Jun. 2, 2021 (5 pages).
Office Action issued in the counterpart Japanese Patent Application No. 2018-521011, dated Mar. 23, 2021 (8 pages).
Notification of Reasons for Refusal issued in the JP Patent Application No. 2018-521011, dated Oct. 5, 2021 (7 pages).
Uchikawa et al., "Somatosensory Evoked Magnetic Fields", Japan Soc. ME & BE, Department of Applied Electronics, Faculty of Science & Engineering, Toyko Denki University, Oct. 1992, vol. 30, pp. 61 (1 page).
Sachiko Koyama, "Neural pathway of reading in Japanese language: A magnetoencephalographic study", Department of Integrative Physiology, National Instutite for Physiological Sciences, 1996, pp. 55-58 (4 pages).

* cited by examiner

BIOMAGNETISM MEASURING DEVICE

TECHNICAL FIELD

The present invention relates to a biomagnetism measuring device that uses a magnetic sensor.

BACKGROUND ART

As a magnetic sensor which detects magnetism, there is conventionally known a magneto resistive (MR) sensor which uses a magneto resistive element (MR element). DC resistance acting on the MR element fluctuates according to the strength of the magnetic field. The MR sensor uses the degree of fluctuation of DC resistance to detect magnetic field variance or the presence of magnetic material as a change in voltage.

MR sensors are widely used as magnetic heads in hard disc devices, rotation sensors (encoders) and position sensors. Further, in recent years, the widespread use of mobile devices such as smartphones and tablet devices has led to these mobile devices being provided with orientation sensors having MR sensors which use geomagnetism to measure orientation. The information obtained from the orientation sensor is used for navigation which uses location information obtained by a global positioning system (GPS).

However, highly sensitive magnetic detection technology is not required for such industrial applications. For example, in rotation sensors and position sensors, highly sensitive magnetic detection is not required because magnets and the like are used as reference signals. Further, orientation sensors do not require highly sensitive magnetic detection because it is enough to detect absolute azimuth with geomagnetism as a reference.

Incidentally, for medical applications, biomagnetism measuring devices such as cerebral magnetometers, magneto cardiograms and muscular magnetometers which detect weak, low frequency magnetism generated by electrical activity in the brain, heart or muscles in a body have been used in recent years. Brain magnetism generated by electrical activity in the brain is approximately $1/100$ million the strength of geomagnetism, and cardiomagnetism generated by electrical activity of the heart is approximately 1/1 million the strength of geomagnetism. Because of this, the magnetic sensors used to detect magnetism generated by the body (hereinafter also referred to as "biomagnetism") are required to have extremely precise detection ability.

As a high-precision magnetic sensor which can is capable of highly precise magnetic detection, there is known a superconducting quantum interference device (hereinafter also referred to as "SQUID") (see, for example, Patent Document 1).

A SQUID sensor is a magnetic sensor that uses the phenomenon of superconductivity and has a Josephson junction. Because of this, SQUID sensors need to be cooled with a refrigerant such as liquid helium or liquid nitrogen during use. Therefore, SQUID sensors must be provided in a dewar that stores refrigerant, which makes it difficult for SQUID sensors to make close contact with a body for detection of biomagnetism.

Further, a plurality of the SQUID sensors are arranged in an array inside the dewar. However, the SQUID sensors must be arranged such that the Josephson junctions inside the SQUID sensors are not electromagnetically affected. Therefore, it is difficult to change the arrangement of SQUID sensors and replace or remove SQUID sensors.

Therefore, SQUID sensors have a problem in that, despite being high-precision magnetic sensors, they cannot be used close enough to the body and are difficult to handle.

In light of this, there has been proposed a biomagnetism measuring device which uses MR sensors that can detect slight magnetism at room temperature, thereby eliminating the need for cooling. For example, in Patent Document 2, there is proposed a biomagnetism measuring device in which a covering member which shields the body from an external magnetic field is formed into a helmet shape or a cylindrical shape, and MR sensors are provided inside the covering member in an array. With this biomagnetism measuring device which uses MR sensors, there is no need to dispose the MR sensors in a dewar and the MR sensors are easier to handle and can be brought closer to the body compared to a device which uses SQUID sensors.

Patent Document 1: Japanese Unexamined Patent Application, Publication No. 2012-020143

Patent Document 2: Japanese Unexamined Patent Application, Publication No. 2012-095939

DISCLOSURE OF THE INVENTION

Problems to be Solved by the Invention

However, if the MR sensors are fixed in place as in the biomagnetism measuring device described in Patent Document 2, the MR sensors may not be able to detect magnetism depending on the subject to be measured (body) because of reduced contact between the subject to be measured and the MR sensors. For example, optimal MR sensor positions will be different for a subject to be measured that has a body shape different to that of a human, such as an animal. In addition, the resolution of required measurement results and optimal positions of the MR sensors will differ depending on the site to be measured.

It is an object of the present invention to provide a biomagnetism measuring device with which magnetic sensors can be disposed at optimal positions according to the object to be measured.

Means for Solving the Problems

The inventors of the present invention carried out extensive research in order to solve the above-mentioned problem. As a result, the inventors found that it is possible to provide a biomagnetism measuring device with which magnetic sensors can be disposed at optimal positions according to the object to be measured by holding a plurality of magnetic sensors such that the magnetic sensors can be removed or moved. Thus, the inventors completed the present invention. More specifically, the present invention provides the following.

(1) The present invention is a biomagnetism measuring device including a plurality of magnetic sensors configured to detect biomagnetism; and holding portions which removably or movably hold the plurality of magnetic sensors such that the plurality of magnetic sensors oppose a body.

(2) The present invention is the biomagnetism measuring device of (1), in which frames are arranged in an array in the holding portion, the frames holding the plurality of magnetic sensors such that the plurality of magnetic sensors can be removed.

(3) The present invention is the biomagnetism measuring device of (1), in which rails are arranged in an array in the holding portion, the rails holding the plurality of magnetic sensors such that the plurality of magnetic sensors can be slidably moved.

(4) The present invention is the biomagnetism measuring device of any of (1) to (3), in which the holding portion is made of a nonmagnetic material.

(5) The present invention is the biomagnetism measuring device of any of (1) to (4), in which the holding portion is made of a flexible material.

(6) The present invention is the biomagnetism measuring device of any of (1) to (5), in which the magnetic sensors are disposed directly below a site to be measured.

Effects of the Invention

According to the present invention, there can be provided a biomagnetism measuring device with which magnetic sensors can be disposed at optimal positions according to the object to be measured.

PREFERRED MODE FOR CARRYING OUT THE INVENTION

An embodiment of the present invention is described in detail below, but the present invention is not limited to the following embodiment and may be changed as appropriate without departing from the object of the present invention.
<Biomagnetism Measuring Device 1>

Figure 1:
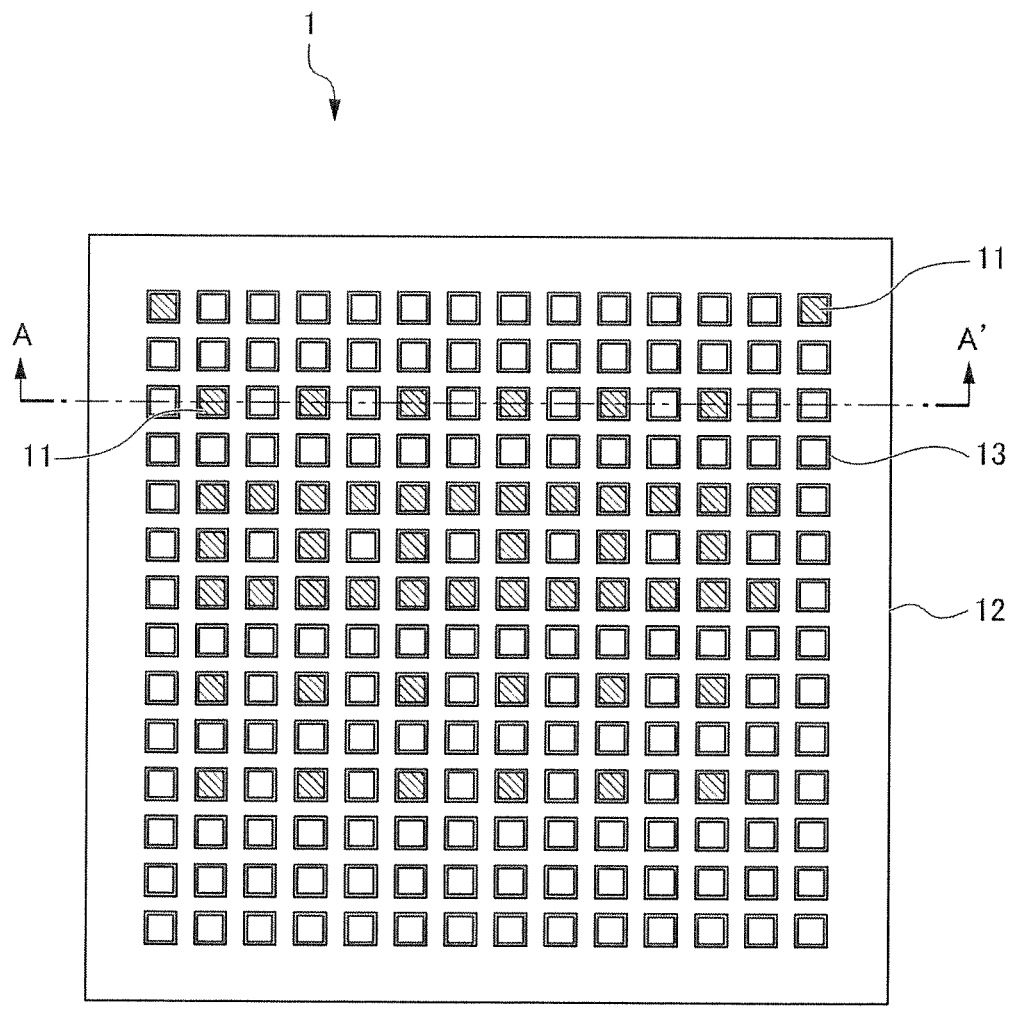
FIG. 1 is a plan view for illustrating an exemplary configuration of a biomagnetism measuring device according to an embodiment of the present invention.
Figure 2:
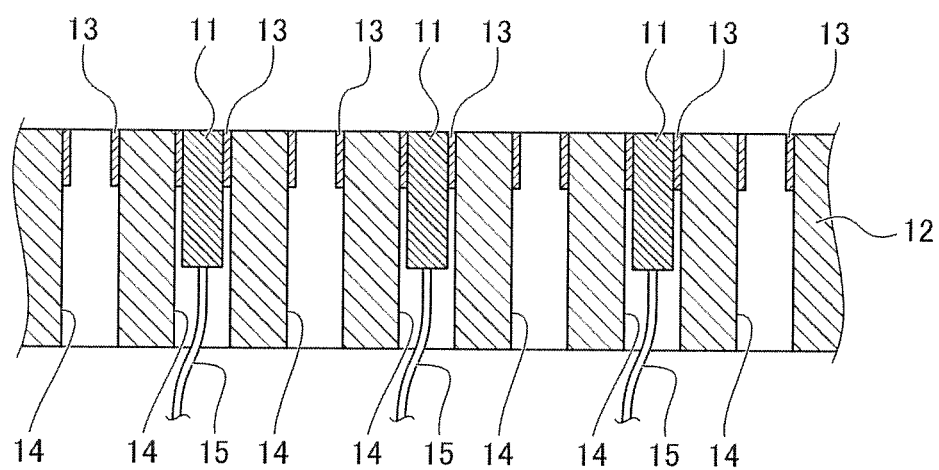
FIG. 2 is a partially expanded view taken long the line A-A' in the biomagnetism measuring device in FIG. 1.
Figure 3:
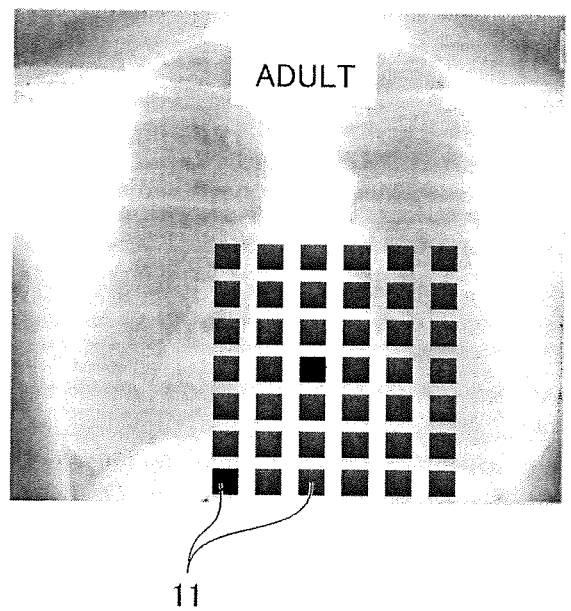
FIG. 3 is an explanatory diagram which shows an X-ray image of an adult subject overlaid with an arrangement diagram of magnetic sensors.
Figure 4:
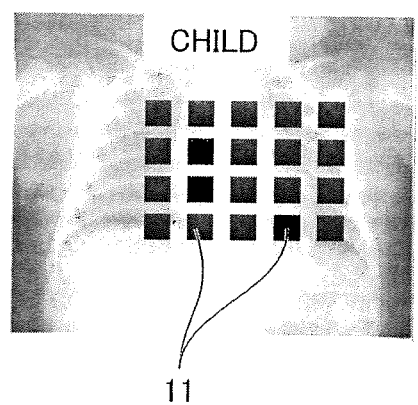
FIG. 4 is an explanatory diagram which shows an X-ray image of a child subject overlaid with an arrangement diagram of magnetic sensors.
Figure 5:
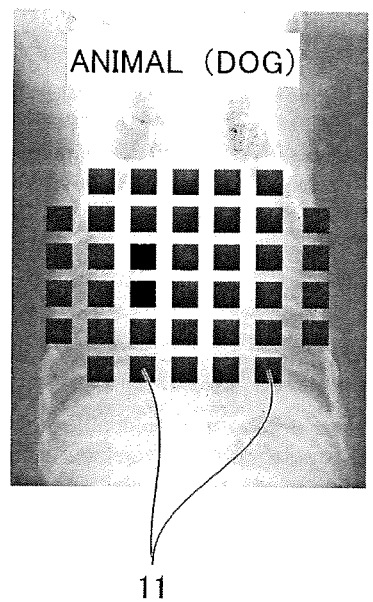
FIG. 5 is an explanatory diagram which shows an X-ray image of a dog subject overlaid with an arrangement diagram of magnetic sensors.

FIG. 1 is a plan view for illustrating an example of a biomagnetism measuring device according to an embodiment of the present invention. FIG. 2 is a partially expanded view taken long the line A-A' in the biomagnetism measuring device in FIG. 1. As illustrated in FIG. 1, the biomagnetism measuring device 1 includes a plurality of magnetic sensors 11 configured to detect biomagnetism and a holding portion 12 which removably holds the magnetic sensors 11. Frames 13 which removably hold the magnetic sensors 11 are arranged in an array in the holding portion 12.

[Magnetic Sensor 11]

The magnetic sensors 11 are configured to detect a magnetic field generated by a body to be measured (hereinafter referred to as "subject"). Examples of the type of sensor used as the magnetic sensor 11 include a giant magnetoresistance sensor (GMR sensor), a tunnel magneto resistance sensor (TMR sensor), an anisotropic magneto resistive sensor (AMR sensor), magnetic impedance sensor (MI sensor) and a fluxgate sensor. The magnetic sensor 11 used in this embodiment may be any kind of magnetic sensor provided that the magnetic sensor can detect a magnetic field (normal component) between about $10^{-4}$ T (tesla) and $10^{-10}$ T (tesla). The magnetic sensor 11 used in this embodiment can acquire the same amount of information as a SQUID sensor, can be used at room temperature and does not need to be disposed in a dewar that stores refrigerant. In addition, the magnetic sensors 11 can be brought closer to a body and are easier to handle than when SQUID sensors are used.

The magnetic sensors 11 may or may not have wiring for receiving signals and power supply. However, because the plurality of magnetic sensors 11 are disposed in the biomagnetism measuring device 1, the biomagnetism measuring device 1 preferably includes wiring 15 as illustrated in FIG. 2 in order to prevent complex wiring.

Signals detected by the magnetic sensors 11 are sent to a calculation unit (not shown). The calculation unit generates biomagnetic information from the signals detected by the magnetic sensors 11 and visualizes and outputs this information to a display device.

[Holding Portion 12/Frame 13]

As illustrated in FIG. 1, the frames 13 are disposed in an array (14×14) in the holding portion 12. The frames 13 are configured to removably hold the magnetic sensors 11. As illustrated in FIG. 2, a plurality of through holes 14 which accept insertion of the magnetic sensors 11 are formed in the holding portion 12, and the frames 13 which removably hold the magnetic sensors 11 are attached to openings which oppose the measurement subject of the through hole 14. The magnetic sensors 11 are not attached to the frames 13 using any particular mechanism and may be attached using a fixing tool such as a screw. With this configuration, the magnetic sensors 11 can be removed to the holding portion 12 and the frames 13 such that detection surfaces of the magnetic sensors 11 oppose a body.

The above-described holding portion 12, frame 13 and fixing tools (not shown) are preferably made of a plastic material such as an acrylic resin, a nonferrous metal such as copper or brass, or a nonmagnetic material such as wood. Forming the holding portion 12, the frames 13 and the fixing tools of a nonmagnetic material can suppress fluctuation in environmental magnetism even if the holding portion 12, the frames 13 and the fixing tools vibrate due to the subject moving, for example, breathing. Therefore, the influence of fluctuation in environmental magnetism on the magnetic sensors 11 can be suppressed.

[Measurement Procedure of Biomagnetism]

The procedure of measuring biomagnetism using the biomagnetism measuring device 1 with the above-described configuration is described with reference to FIGS. 3 to 7.

First, the person conducting the measurement determines the number of magnetic sensors 11 required and the positions of the magnetic sensors 11 according to the subject to be measured, for example, the stature of the subject or the site and attaches the predetermined magnetic sensors 11 at optimal positions on the frames 3 in the holding portion 2 of the biomagnetism measuring device 1. If the magnetic sensors 11 include the wiring 15 for receiving signals, the magnetic sensors 11 may be inserted into the through holes 14 from beneath the holding portion 12 and attached to the frames 13 using the fixing tools.

For example, if using the biomagnetism measuring device 1 to obtain a magneto cardiogram and the subject is an adult, 42 magnetic sensors 11 should be attached to an array of 6×7 frames 13 (see FIG. 3) of the frames 13 arranged in a 14×14 array. If the subject is a child, 20 magnetic sensors 11 should be attached to an array of 5×4 frames 13 (see FIG. 4) of the frames 13 arranged in a 14×14 array. If the subject is a dog, 38 magnetic sensors 11 should be attached to an array of 5×1+7×4+5×1 frames 13 (see FIG. 5) of the frames 13 arranged in a 14×14 array. Among the frames 13 arranged in a 14×14 array on the holding portion 12, the positions of the frames 13 selected in order to attach the magnetic sensors 11 may be at a central portion or a peripheral portion of the holding portion 12 but are preferably at a central portion in consideration of improving stability of the subject.

Depending on the site of the patient, the resolution of required measurement results may differ. In this case, as illustrated in FIG. 1, the magnetic sensors 11 may be concentrated at positions that require high resolution results and may be dispersed at positions that do not require high resolution results.

Then, the person conducting the measurement guides the subject so that the site to be measured is placed on the biomagnetism measuring device 1 disposed with the magnetic sensors 11 and checks if the detection surfaces of the magnetic sensors 11 are in close contact with the site to be measured. Then, the person conducting the measurement operates the biomagnetism measuring device 1 using an operation unit (not shown) and starts the measurement. Further, after guiding the subject so that the site to be measured is placed on the biomagnetism measuring device 1 disposed with the magnetic sensors 11, the person conducting the measurement may readjust the arrangement of the magnetic sensors 11 while confirming that the detection surfaces of the magnetic sensors 11 are in close contact with the site to be measured on the basis of the detection results of the magnetic sensors 11 by operating the biomagnetism measuring device 1.

In terms of improving contact between the detection surfaces of the magnetic sensors 11 and the site to be measured, the magnetic sensors 11 are preferably disposed directly below the site to be measured. Therefore, for example, a subject 100 may lay face up on an examination table 2 embedded with the biomagnetism measuring device 1 (see FIG. 6). Alternatively, the subject 100 may lay face down on the examination table 2 (see FIG. 7). Through the subject 100 laying down on the examination table 2 embedded with the biomagnetism measuring device 1, gravity works on the subject 100 to improve contact between the body surface of the subject 100 and the detection surfaces of the magnetic sensors 11. As a result, the biomagnetism measuring device 1 can obtain more accurate biomagnetic information.

In this way, through arranging the magnetic sensors 11 at the optimal positions according to the stature and the site of the subject (body), biomagnetic information can be obtained in the optimal area. As a result, trouble such as biomagnetic information not being obtained due to lack of contact between the magnetic sensors 11 and the body is prevented.

In addition, because only the required magnetic sensors 11 are arranged, signal reception and power supply to unnecessary magnetic sensors 11 does not occur and power and costs can be saved.

By attaching the magnetic sensors 11 at the optimal positions according to the required resolution of measurement results, the number of magnetic sensors 11 required can be reduced. As a result, signal reception and power supply to unnecessary magnetic sensors 11 does not occur and power and costs can be saved.

Modification Example of Biomagnetism Measuring Device

Modification examples of the biomagnetism measuring device according to this embodiment are described below with reference to FIGS. 8 to 10. Note that in FIGS. 8 to 10, components that are the same as above-described components are denoted by the same reference symbols and descriptions thereof are omitted.

First Modification Example

Figure 8:
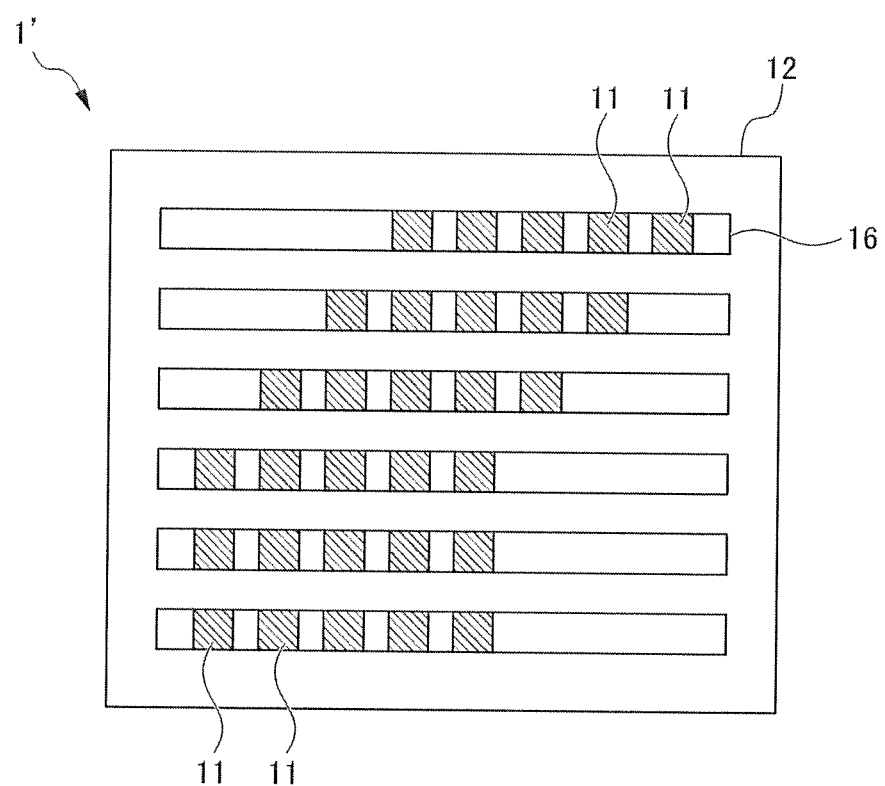
FIG. 8 is a plan view for illustrating a first modification example of the biomagnetism measuring device, in which a holding portion is provided with a rail.

FIG. 8 illustrates a first modification example of the biomagnetism measuring device. In the biomagnetism measuring device 1 illustrated in FIGS. 1 and 2, the magnetic sensors 11 are removably held by the frames 13 in the holding portion 12, but the magnetic sensors 11 may be movably held by rails 16.

(Rail 16)

In the biomagnetism measuring device 1' illustrated in FIG. 8, a plurality of rails 16 which movably hold the magnetic sensors 11 are formed in parallel in the holding portion 12. With this configuration, the plurality of magnetic sensors 11 can be moved to arbitrary positions along the rails 16. The number of magnetic sensors 11 and rails 16 is not particularly limited and may be chosen as appropriate depending on the site to be measured. The magnetic sensors 11 may or may not be removable from the rails 16.

Similar to the holding portion 12, the rails 16 are preferably made of a plastic material such as an acrylic resin, a nonferrous metal such as copper or brass, or a nonmagnetic material such as wood. Forming the holding portion 12 and the rails 16 of a nonmagnetic material can suppress fluctuation in environmental magnetism even if the holding portion 12 and the rails 16 vibrate due to the subject moving, for example, breathing. Therefore, the influence of fluctuation in environmental magnetism on the magnetic sensors 11 can be suppressed.

With the biomagnetism measuring device 1' formed with the rails 16 in the holding portion 12, the person conducting the measurement can easily move the magnetic sensors 11 along the rails 16 while checking measurement results when measuring biomagnetism of the subject. In other words, with the biomagnetism measuring device 1' formed with the rails 16 in the holding portion 12, it is easy align the magnetic sensors 11 during measurement.

Second Modification Example

Figure 9:
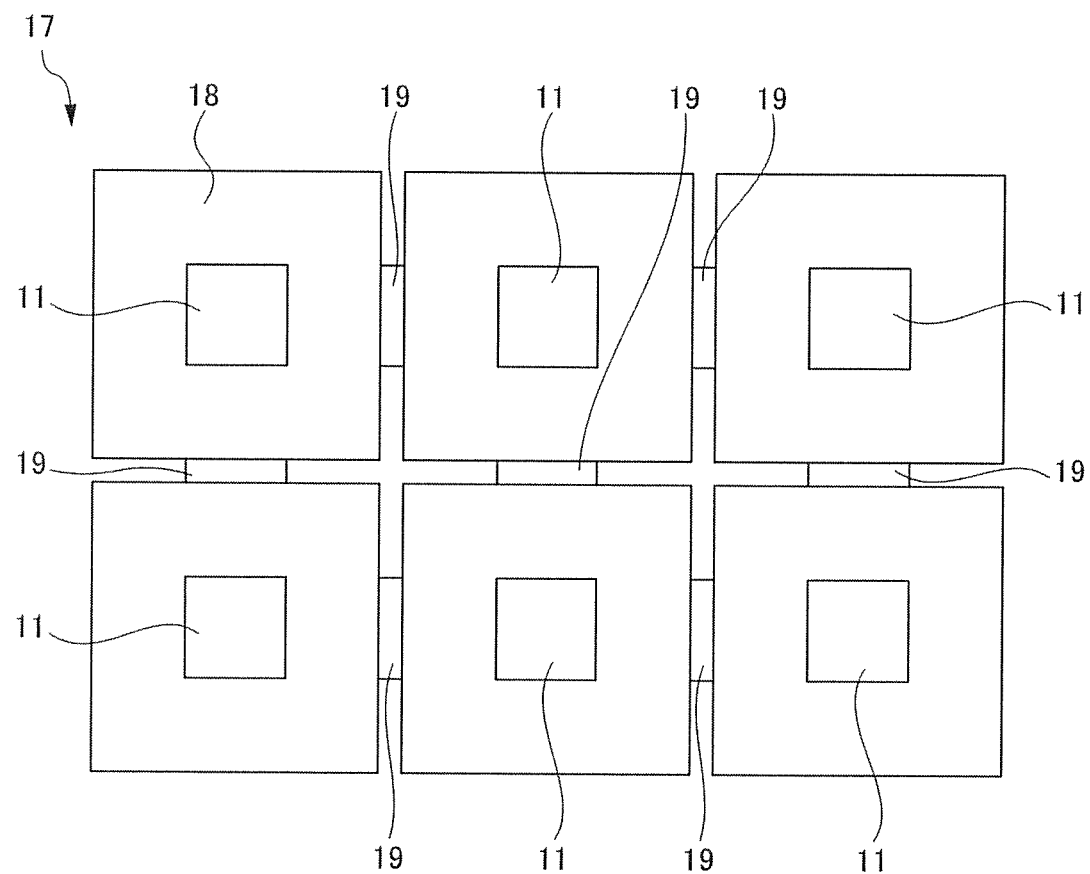
FIG. 9 is a plan view for illustrating a second modification example of the biomagnetism measuring device, in which the holding portion is made of a flexible material.

FIG. 9 illustrates a second modification example of the biomagnetism measuring device. Although the above-described holding portion 12 is a molded body integrally molded with a nonmagnetic material such as plastic, a holding portion 17 may be made of a flexible material.

The holding portion 17 illustrated in FIG. 9 includes a plurality of fixing portions 18 which individually fix the plurality of magnetic sensors 11 and hinges 19 which link the plurality of fixing portions 18 to each other. By forming the hinges 19 of a flexible material such as rubber, the magnetic sensors 11 can be arranged on the holding portion 17 according to the shape of the body even if the body is uneven or curved, and the detection surfaces of the magnetic sensors 11 can make close contact with the body surface of the body. As a result, the biomagnetism measuring device including the holding portion 17 can accurately measure biomagnetism. Note that the fixing portions 18 may also be made of a flexible material provided that the fixing portions 18 can fix the magnetic sensors 11.

Third Modification Example

Figure 6:
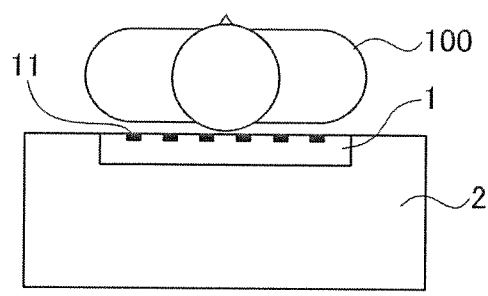
FIG. 6 is an explanatory diagram for explaining a configuration in which the magnetic sensors are disposed directly below a subject.
Figure 7:
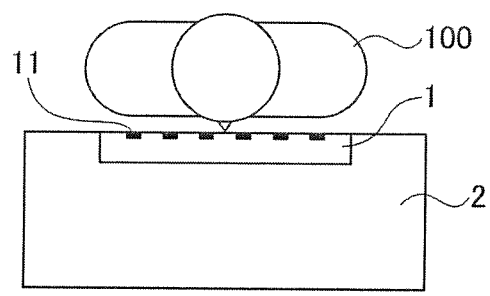
FIG. 7 is an explanatory diagram for explaining another configuration in which the magnetic sensors are disposed directly below a subject.
Figure 10:
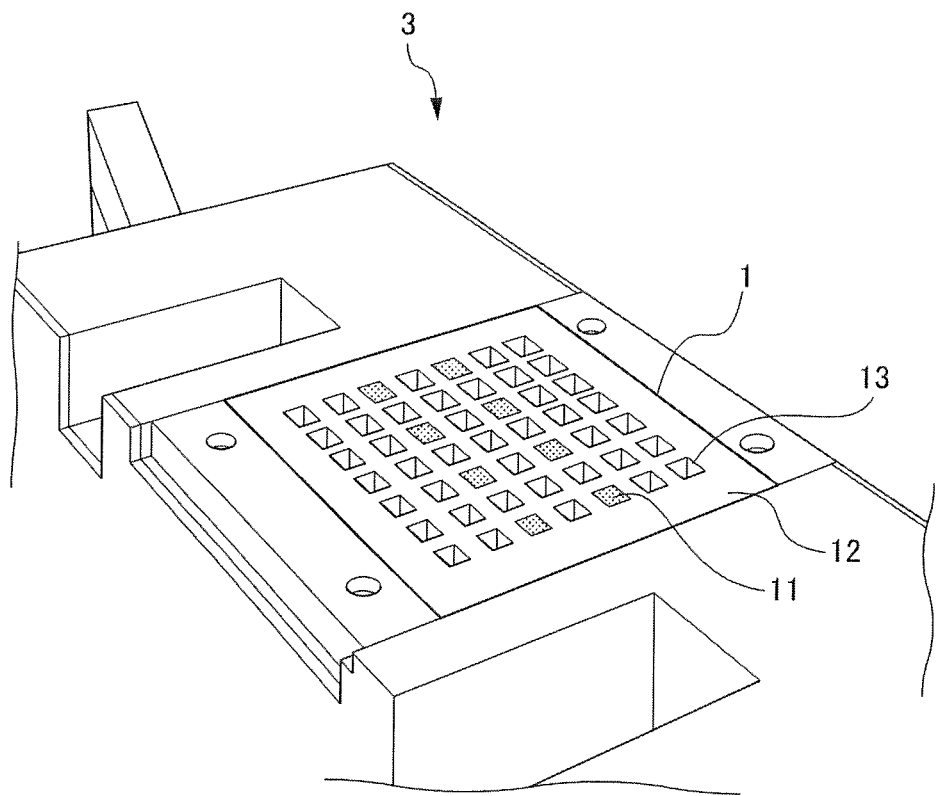
FIG. 10 is a perspective view for illustrating a third modification example of the biomagnetism measuring device in which a table provided with the biomagnetism measuring device has been replaced with that having another configuration.

FIG. 10 illustrates a third modification example of the biomagnetism measuring device. Although the biomagnetism measuring device 1 illustrated in FIGS. 6 and 7 is embedded into an examination table which the subject 100 lies on, the table into which the biomagnetism measuring device 1 is embedded is not limited thereto.

For example, if the site to be measured is part of a limb of the subject (for example, a hand), as illustrated in FIG. 10, the biomagnetism measuring device 1 may be embedded into a measurement table 3 which is smaller than the examination table 2. With the measurement table 3 illustrated in FIG. 10, magnetism generated from the hand can be detected without the subject lying down on the table, and the magnetic sensors 11 can be attached at the optimal positions according to the size of the hand and the required resolution.

EXPLANATION OF REFERENCE NUMERALS 1 biomagnetism measuring device
2 examination table
3 measurement table
11 magnetic sensor
12 holding portion
13 frame
14 through hole
15 wiring
16 rail
17 holding portion
18 fixing portion
19 hinge

The invention claimed is:
1. A biomagnetism measuring device comprising:
a plurality of magnetic sensors configured to detect biomagnetism, wherein the biomagnetism measuring device is configured to be embedded in an examination table;
holding portions; and
a plurality of frames arranged in an array in the holding portions and being configured to removably hold the plurality of magnetic sensors such that the plurality of magnetic sensors are opposed to a trunk of a living body,
wherein the plurality of magnetic sensors have a plurality of detection surfaces that are configured to face the trunk of the living body lying on the examination table such that contact between the trunk of the living body and the plurality of detection surfaces of the plurality of magnetic sensors is improved by gravity acting on the trunk of the living body,
wherein the plurality of magnetic sensors are giant magnetoresistance sensors (GMR sensors), anisotropic magneto resistive sensors (AMR sensors), magnetic impedance sensors (MI sensors), or fluxgate sensors,
wherein the number and position of the plurality of magnetic sensors required for measurement of the trunk of the living body in a state where the plurality of magnetic sensors are held by the plurality of frames and in terms of a horizontal plane direction are two-dimensionally changeable according to a stature of the trunk of the living body and a site of the trunk of the living body, and
wherein a subset of the plurality of frames actually holds the plurality of magnetic sensors, the subset constituting less than all of the plurality of frames in the holding portions.

2. The biomagnetism measuring device according to claim 1, wherein the holding portion is made of a flexible material.

3. The biomagnetism measuring device according to claim 1, wherein the holding portions comprise a plurality of fixing portions and a plurality hinges connecting adjacent fixing portions among the plurality of fixing portions, and wherein a respective fixing portion among the plurality of fixing portions holds a respective magnetic sensor among the plurality of magnetic sensors.

4. The biomagnetism measuring device according to claim 1, further comprising a fixing tool that couples a respective magnetic sensor among the plurality of magnetic sensors to a respective frame among the frames, the fixing tool being a screw.

5. The biomagnetism measuring device according to claim 1, further comprising a plurality of rails arranged in an array, wherein a rail among the plurality of rails is configured to hold a portion of the plurality of magnetic sensors such that the portion is slidably moveable.

6. The biomagnetism measuring device according to claim 1, wherein the holding portion is made of a nonmagnetic material.

7. The biomagnetism measuring device according to claim 6, wherein the holding portion is made of a flexible material.

8. A biomagnetism measuring system comprising:
an examination table; and
a biomagnetism measuring device embedded in the examination table,
wherein the biomagnetism measuring device comprises a plurality of magnetic sensors configured to detect biomagnetism, holding portions, and a plurality of frames arranged in an array in the holding portions and being configured to removably hold the plurality of magnetic sensors such that the plurality of magnetic sensors are opposed to a trunk of a living body,
wherein the plurality of magnetic sensors have detection surfaces that are configured to face the trunk of the living body lying on the examination table such that contact between the trunk of the living body and the detection surfaces of the plurality of magnetic sensors is improved by gravity acting on the trunk of the living body,
wherein the plurality of magnetic sensors are giant magnetoresistance sensors (GMR sensors), anisotropic magneto resistive sensors (AMR sensors), magnetic impedance sensors (MI sensors), or fluxgate sensors,
wherein the number and the position of magnetic sensors required for measurement of the trunk of the living body in a state where the plurality of magnetic sensors are held by the plurality of frames and in terms of a horizontal plane direction are two- dimensionally changeable according to a stature of the trunk of the living body and a site of the trunk of the living body, and wherein a subset of the plurality of frames actually holds the plurality of magnetic sensors, the subset constituting less than all of the plurality of frames in the holding portions.

9. The biomagnetism measuring system according to claim 8, wherein the holding portion is made of a flexible material.

10. The biomagnetism measuring system according to claim 8, wherein the examination table comprises a plurality of through holes configured to accept insertion of the plurality of magnetic sensors, and wherein the plurality of through holes is greater than the plurality of magnetic sensors.

11. The biomagnetism measuring system according to claim 8, wherein the holding portion is made of a nonmagnetic material.

12. The biomagnetism measuring system according to claim 11, wherein the holding portion is made of a flexible material.

\* \* \* \* \*